United States Patent
Eguchi et al.

(10) Patent No.: US 6,186,010 B1
(45) Date of Patent: Feb. 13, 2001

(54) BOLT FOR ULTRASONIC AXIAL TENSION MEASUREMENT

(75) Inventors: Takashi Eguchi, Toyota; Tomoji Sakai, Okazaki; Tatsuyuki Aoki, Toyota, all of (JP)

(73) Assignee: Toyota Jidosha Kabushiki Kaisha, Toyota (JP)

( * ) Notice: Under 35 U.S.C. 154(b), the term of this patent shall be extended for 0 days.

(21) Appl. No.: 09/210,589

(22) Filed: Dec. 15, 1998

(30) Foreign Application Priority Data

Dec. 17, 1997 (JP) .................................................. 9-347647

(51) Int. Cl.⁷ ...................................................... F16B 31/02
(52) U.S. Cl. ................................................. 73/761; 73/597
(58) Field of Search ............................. 73/761, 597, 599; 411/504, 533

(56) References Cited

U.S. PATENT DOCUMENTS

| | | | |
|---|---|---|---|
| 3,630,116 | * 12/1971 | Harper .................................. | 411/504 |
| 3,748,948 | * 7/1973 | Schmitt ................................. | 411/378 |
| 4,502,826 | * 3/1985 | Fafard .................................. | 411/340 |
| 5,029,480 | 7/1991 | Kibblewhite . | |
| 5,131,276 | * 7/1992 | Kibblewhite ......................... | 73/761 |
| 5,222,852 | * 6/1993 | Snyder ................................. | 411/553 |
| 6,009,759 | * 1/2000 | Kibblewhite et al. ................. | 73/761 |

FOREIGN PATENT DOCUMENTS

| | | |
|---|---|---|
| 60-194473 | 12/1985 | (JP) . |
| 07229798 | 8/1995 | (JP) . |
| 07280677 | 10/1995 | (JP) . |
| 97/44644 | 11/1997 | (WO) . |

OTHER PUBLICATIONS

Bartsch, C.: "Sichere Vorspannkraftkontrolle von Schraubenvergindungen durch Ultraschall", In: Antriebstechnik 33 (1994) Nr. 12, S. 38, 39.

Werthe, B.: "Vorspannkraftgesteuerte Schraubenmontage durch Ultraschall", Sep. 5, 1997, Volkswagen Nutzfahrzeuge, S. 1–21.

* cited by examiner

*Primary Examiner*—Max Noori
(74) *Attorney, Agent, or Firm*—Burns, Doane, Swecker, & Mathis, LLP

(57) ABSTRACT

Both end surfaces of a head portion and an axial portion of a bolt are formed into a curved surface having a predetermined curvature in order to provide a bolt which allows accurate axial tension measurement without changing various settings of an axial tension detection device. Upon ultrasonic radiation applied from a piezoelectric element into a top surface of a head portion of the bolt, the top surface thereof serves as an ultrasonic lens to allow ultrasonic propagation in convergence within the bolt. If the bottom end surface of the axial portion of the bolt is formed into a curved surface, the bottom end surface thereof will also serve as the ultrasonic lens to allow propagation of the reflection to return to the piezoelectric element in convergence. The ultrasonic propagation path within the bolt is not diffused, which allows the ultrasonic radiation to be reflected from the bottom surface of the axial portion of the bolt so as to be detected by the piezoelectric element. The axial tension, thus, can be measured with great accuracy.

7 Claims, 6 Drawing Sheets

BOLT FOR ULTRASONIC AXIAL TENSION MEASUREMENT

INCORPORATION BY REFERENCE

The disclosure of Japanese Patent Application No. HEI 9-347647 filed on Dec. 17, 1997 including the specification, drawings and abstract is incorporated herein by reference in its entirety.

BACKGROUND OF THE INVENTION

1. Field of the Invention

The present invention relates to a bolt and, more particularly, to one adapted to ultrasonic axial tension measurement. The term "axial tension" used herein stands for a tightening force generated in the tightened bolt in its axial direction.

2. Description of the Related Art

It has been a conventional practice to conduct ultrasonic measurement of the axial tension generated in the tightened bolt in the axial direction for secure bolt tightening. The aforementioned axial tension measurement is conducted through ultrasonic radiation to one end surface of the bolt and detection of reflection (echo) from the other end surface of the bolt in the axial direction. The axial tension generated in the bolt will be measured based on the detected results. Referring to FIG. 3, the time taken from ultrasonic radiation to detection of the reflection before tightening the bolt (FIG. 3A) is shorter than that after tightening the bolt (FIG. 3B) by the time t owing to generation of the axial tension in the bolt. The time difference t will vary in proportion to the axial tension. Accordingly the time taken from ultrasonic radiation to reflection detection has been conventionally measured so as to measure the axial tension.

An axial tension measurement device is generally formed of a piezoelectric element which is mounted to a head of the bolt for ultrasonic radiation thereto and detection of reflection. This device has been applied to a bolt tightening device such as a nut runner which rotates a socket engaged with the bolt head for rotation. The bolt tightening device is driven while the axial tension generated in the bolt is measured by the axial tension measurement device. When it is detected that the axial tension reaches a target value, operation of the bolt tightening device is stopped. In this way, the bolt can be tightened such that a constant axial tension is generated.

Referring to FIG. 5, both a top surface 22a of a head portion 22 to which ultrasonic radiation is applied from a piezoelectric element 31 and a bottom surface 23a of an axial portion 23 of a generally employed bolt 21 as the other end surface thereof in an axial direction from which the ultrasonic radiation is reflected have substantially flat surfaces. As a result, each propagation path of both the ultrasonic radiation and the reflection will be diffused within the axial portion 23 (as shown by an arrow Uwa in FIG. 6). The time taken by the diffused reflection to reach the piezoelectric element 31 may vary depending on the propagation path. As a result, a plurality of different reflections are detected.

Referring to FIG. 5, the generally employed bolt 21 is formed such that a sectional area (diameter) d1 of the head portion 22 to be engaged with a socket (not shown) of the bolt tightening device is larger than the sectional area (diameter) d3 of the axial portion 23 that has been threaded. Accordingly all the ultrasonic radiation applied to the head portion 22 is not always reflected from a bottom surface 23a of the axial portion 23. That is, detected reflection may include the one reflected from the end surface 22b of the radially extended portion of the head portion 22 (as shown by an arrow Uwb in FIG. 5). Referring to FIG. 7, it is difficult to distinguish the reflection from the bottom surface 23a of the axial portion 23 from those of a plurality of detected reflections Uwa. Furthermore, the reflection Uwb from the end surface 22b of the extended portion of the head portion 22 of the bolt 21 may be a cause of noise, thus degrading accuracy of the axial tension measurement.

On the foregoing ground, publication of Japanese Utility Model No. SHO 60-194473 discloses a device for detecting axial tension of a bolt incorporating an ultrasonic transducer disposed in close proximity to the top surface of the bolt head for ultrasonic radiation into the bolt. In the aforementioned device, an ultrasonic lens for converging ultrasonic radiation from the ultrasonic transducer to the top surf ace of the bolt head is interposed therebetween. A concavity having relatively a large radius of curvature is formed in a back surface of a cap to which the ultrasonic transducer is adhered, which may form a convex-like space having one flat surface defined by the bolt head. A convex ultrasonic lens can be defined by the space filled with oil.

In the aforementioned device for detecting axial tension of the bolt, the ultrasonic lens converges the ultrasonic radiation applied from the ultrasonic transducer to the top surface of the bolt head. The ultrasonic radiation applied into the bolt head is focused to the cross section of the axial portion of the bolt as it propagates from the bolt head to the axial portion. The ultrasonic radiation applied into the bolt head is, thus, efficiently propagated within the axial portion of the bolt. The ultrasonic radiation exhibiting relatively higher intensity can be propagated within the axial portion of the bolt for detecting the ultrasonic propagation time. As a result, the signal level upon receipt of the ultrasonic radiation is raised to a higher level compared with other noise, thus detecting the axial tension of the bolt with high accuracy. The aforementioned generally employed art discloses the description with respect to change in the shape of the space constituting the ultrasonic lens for converging the ultrasonic radiation depending on the sonic speed of propagation between the substance filled in the space and the cap-forming material (ultrasonic propagation characteristics).

However, the length of the bolt subjected to the axial tension measurement is not always constant. Accordingly, in the device for detecting the axial tension of a bolt disclosed in Publication of Japanese Utility Model SHO No. 60-194473, the ultrasonic radiation applied from the ultrasonic transducer to the top surface of the bolt head can be converged by the ultrasonic lens. However, the convergence degree of the ultrasonic radiation applied from the ultrasonic transducer to the top surface of the bolt head may vary. Therefore it is necessary to select the type of the ultrasonic lens, concave or convex (the concavity formed in the back surface of the cap to which the ultrasonic transducer is adhered), lens shape including the curvature, and ultrasonic propagation characteristics such as the material with which the lens-forming space is filled in accordance with the bolt length.

In the above-identified reference, convergence of the ultrasonic radiation applied from the ultrasonic transducer to the top surface of the bolt head is considered. However, the convergence of the ultrasonic reflection from the bottom surface of the axial portion of the bolt is not considered. As the propagation path of the reflection becomes complicated, the reflection is diffused while being detected.

SUMMARY OF THE INVENTION

It is an object of the present invention to provide a bolt adapted to measure axial tension generated therein without changing various settings of the device for detecting the axial tension and to provide an axial tension measurement device for the bolt.

The present invention provides a bolt subjected to ultrasonic axial tension measurement, in which at least one of opposite end surfaces of a head portion and an axial portion of the bolt is formed into a curved surface having a predetermined curvature.

In this invention, a curved surface formed as a top surface of a head portion or a bottom surface of an axial portion of the bolt functions as the ultrasonic lens. If the top surface of the head portion of the bolt is formed into a curved surface, the ultrasonic radiation applied thereto is converged for propagation within the bolt toward the bottom surface of the axial portion. If the bottom surface of the axial portion is formed into a curved surface, the reflection from the bottom surface of the axial portion is converged by the curved surface for returning to the top surface of the head portion of the bolt.

According to the present invention, as at least one of opposite end surfaces of the head portion and the axial portion of the bolt is formed into a curved surface having a predetermined curvature, the axial tension can be measured with great accuracy without changing various settings of the axial tension detection device.

DESCRIPTION OF THE PREFERRED EMBODIMENT

Figure 1:
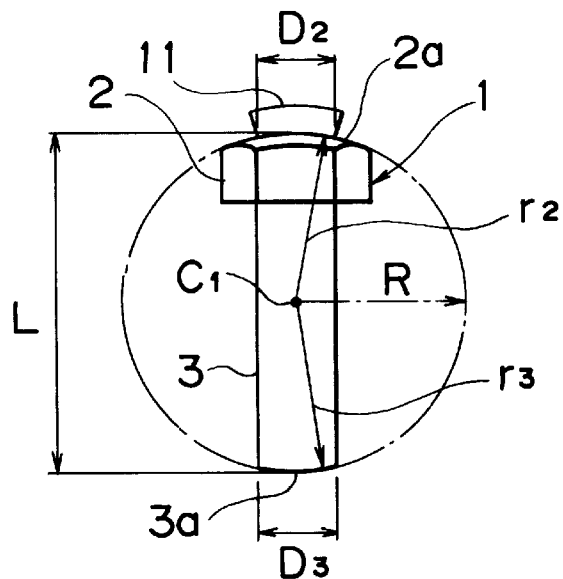
FIG. 1 is a front view showing one embodiment of a bolt according to the present invention.
Figure 2:
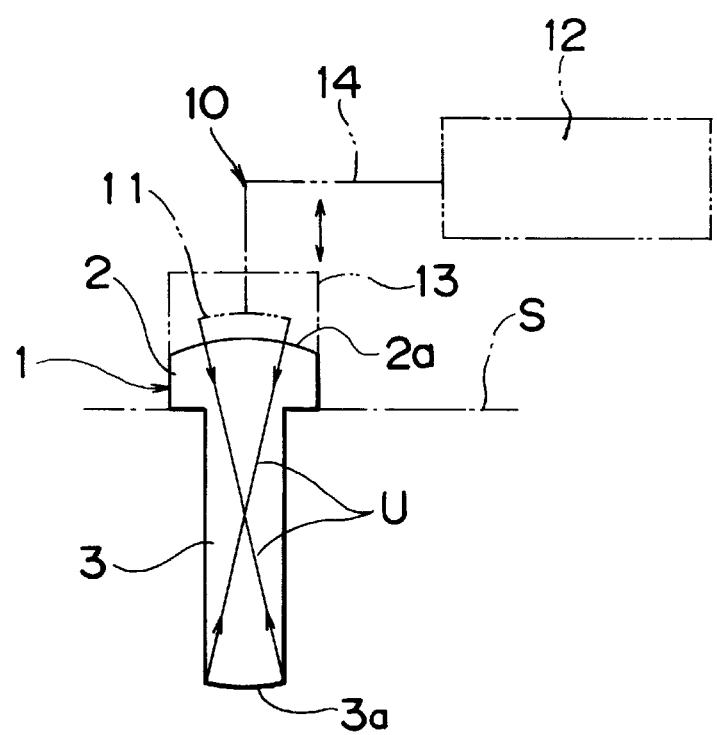
FIG. 2 is an explanatory view of the bolt of FIG. 1 representing propagation both of ultrasonic radiation applied from a piezoelectric element of an axial tension detection device and reflection thereof.

Referring to FIGS. 1 and 2, an embodiment of a bolt according to the present invention will be described in detail. Like reference numerals and designations in the drawings refer to like elements.

A bolt of the present invention is adapted to ultrasonic axial tension measurement. Referring to FIG. 1, a top surface 2a of a head 2 and the opposite bottom surface 3a of a an axial portion 3 of a bolt 1 are formed into curved surfaces each having a predetermined curvature r2 and r3, respectively.

Each of the top surface 2a and opposite bottom surface 3a of the head 2 and axial portion 3 of the bolt 1 forms a portion of a circle having a radius R at a center $C_1$, (=L/2) as a mid point of the distance L (whole length) from the top of the head 2 to the bottom of the axial portion 3 of the bolt 1 in this embodiment. The curvature r2 of the curved surface as the top surface 2a of the head 2 of the bolt 1 is specified such that ultrasonic radiation oscillated by the ultrasonic oscillation element (to be described later) is converged to the bottom surface 3a of the axial portion 3. The curvature r3 of the curved surface as the bottom surface 3a of the axial portion 3 is specified such that the ultrasonic radiation is reflected in convergence to ultrasonic detection means (to be described later). The top surface 2a of the head 2 and end surface 3a of the axial portion 3 are formed through machining process, for example, cutting, grinding and the like after manufacturing the bolt 1 or simultaneously with threading of the axial portion 3. The head 2 of the thus processed bolt 1 is engaged with a socket (not shown) of a tightening device such as a nut runner. The bolt 1 will be screwed to an internal thread of an object S to which the bolt 1 is tightened by rotating to drive the socket for tightening. The axial tension is measured by an axial tension measurement device 10. The tightening device can be controlled based on the measurement results.

The axial tension measurement device 10 is formed of a piezoelectric element 11 which serves as an ultrasonic oscillating element to oscillate ultrasonic radiation to the top surface 2a of the head 2 of the bolt 1 and as ultrasonic detection means to detect reflection thereof, and an ultrasonic oscillation/detection device 12 which causes the piezoelectric element 11 to oscillate ultrasonic radiation and processes signals output thereby upon detection of the reflection.

The element serving as the ultrasonic oscillating element and ultrasonic detection means is not limited to the piezoelectric element. That is, the transducer of electrostrictive type may be used.

The piezoelectric element 11 is disposed in the socket of the tightening device or in a contactor 13 provided separately from the tightening device, which can be brought into abutment on or away from the bolt 1 so as to be in close proximity to the top surface 2a of the head 2 of the bolt 1. The piezoelectric element 11 is connected to the ultrasonic oscillation/detection device 12 via a cable 14. The embodiment may be structured such that the piezoelectric element 11 directly fixed to the top surface 2a of the head 2 of the bolt 1 is detachably connected to the cable 14 of the ultrasonic oscillation/detection device 12 via a connector.

Figure 3A:
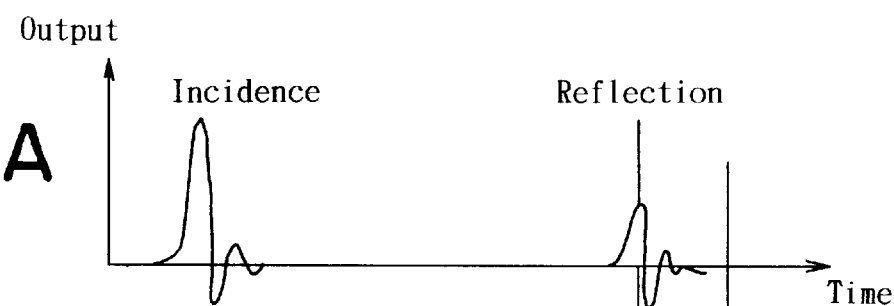
FIGS. 3A and 3B explanatory views, with respect to each case of before and after tightening the bolt, representing the time taken from ultrasonic radiation into the bolt head by the piezoelectric element of the axial tension detection device to detection of the reflection thereby.
Figure 3B:
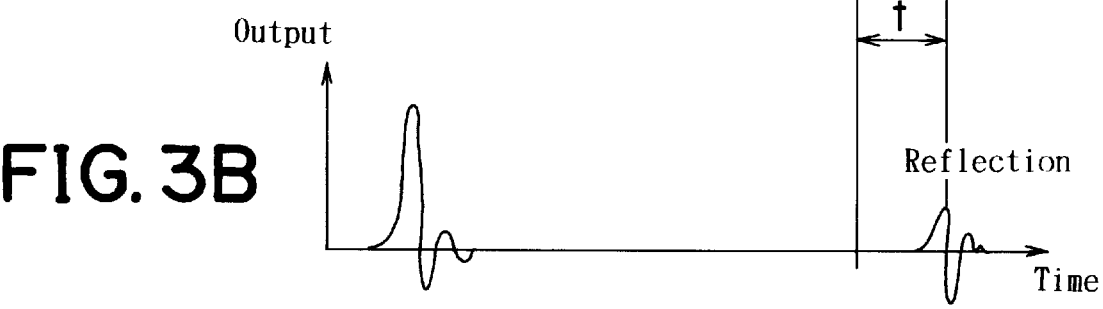

The ultrasonic oscillation/detection device 12 applies high frequency pulse at a predetermined voltage to the piezoelectric element 11 for ultrasonic oscillation. It further amplifies output signals of the piezoelectric element 11 resulting from reflection such that the difference t in time taken from ultrasonic oscillation to detection of reflection (see FIGS. 3A and 3B).

When the ultrasonic oscillation/detection device 12 applies high frequency pulse at a predetermined voltage to the piezoelectric element 1 via the cable 14, ultrasonic radiation is applied into the top surface 2a of the head 2 of the bolt 1 through piezoelectric effect of the piezoelectric element 11. As the top surface 2a of the head 2 of the bolt 1 is curved to function as the ultrasonic lens, the ultrasonic radiation propagates within the bolt 1 while being directed to the bottom surface 3a of the axial portion 3 in convergence as shown by an arrow U in FIG. 2. As the bottom surface 3a of the axial portion 3 is curved to function as the ultrasonic lens, the reflection from the bottom surface 3a of the axial portion 3 likewise propagates back to the piezoelectric element 11 in convergence. In this way, the ultrasonic radiation is securely reflected from the bottom surface 3a of the axial portion 3 without diffusing propagation path of the ultrasonic radiation within the bolt 1, which can be detected by the piezoelectric element 11. This makes it possible to measure the axial tension with great accuracy. Also the present invention eliminates necessity to change various settings such as the shape and material of the component of the contractor 13 of the axial tension detection device 10 according to the length L of the bolt 1 subjected to the axial tension measurement or ultrasonic propagation characteristics of the components. In the embodiment described herein, opposite top and bottom surfaces 2a, 3a of the head 2 and the axial portion 3 of the bolt 1 form the respective portions of a circle having a radius R at a center $C_1$ as a mid point of the whole length L of the bolt 1 (R=r2=r3). Preferably the diameter D2 of the piezoelectric element 11 in a plan view thereof is specified to be substantially equal to or smaller than the diameter D3 of the cross section of the bottom surface 3a of the axial portion 3 of the bolt 1. In the aforementioned structure, the area where the ultrasonic radiation is oscillated by the piezoelectric element 11 becomes equal to the area where the reflection thereof is detected. If the curvature r2 of the curved surface as the top surface 2a of the head 2 is different from the curvature r3 of the curved surface as the bottom surface 3a of the axial portion 3, the diameter D2 of the piezoelectric element 11 in a plan view thereof can be specified according to convergence degree of the ultrasonic radiation at the top surface 2a of the head 2, the diameter D3 of the axial portion 3, and the convergence degree of the ultrasonic radiation reflected from the bottom surface 3a of the axial portion 3.

Figure 4:
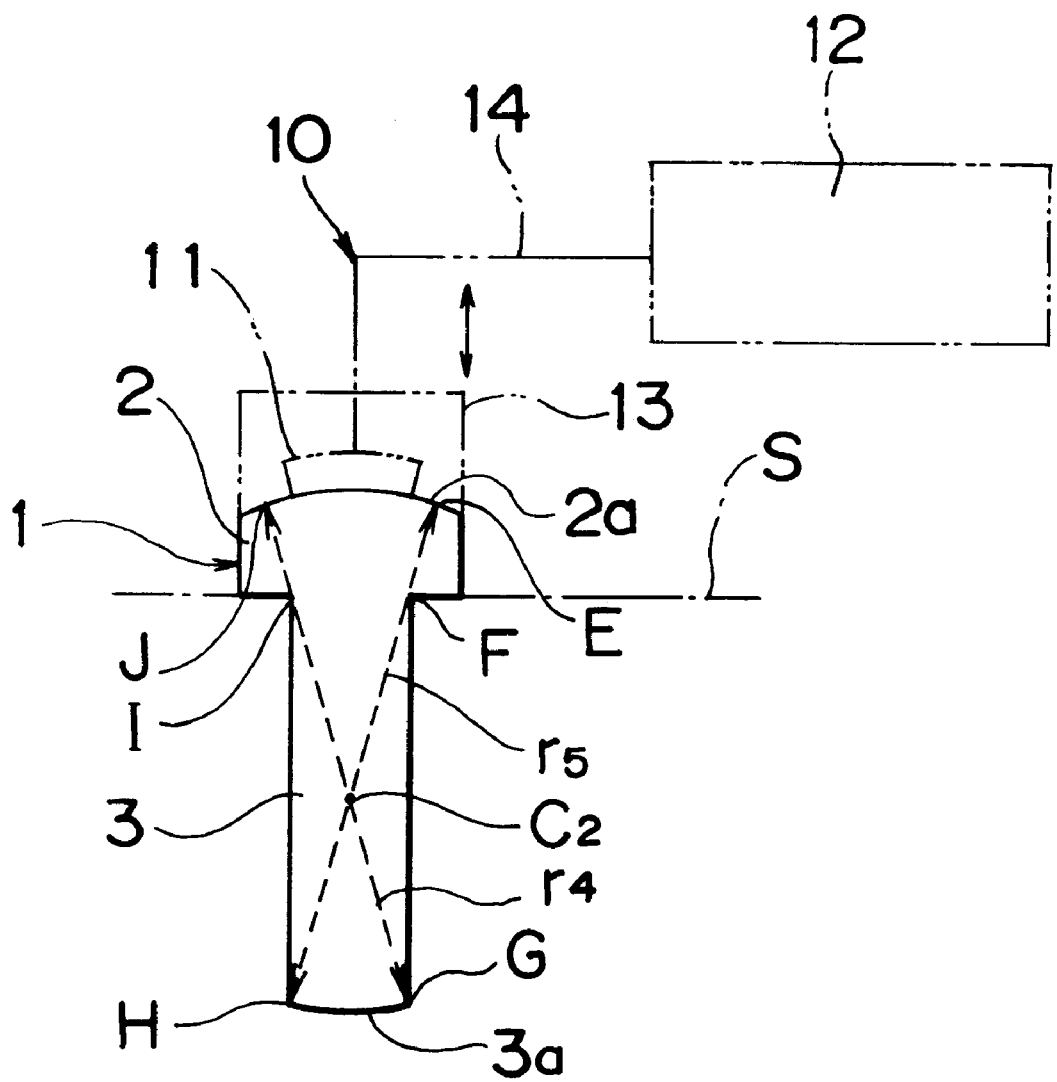
FIG. 4 is an explanatory view representing another embodiment of the bolt of the present invention.
Figure 5:
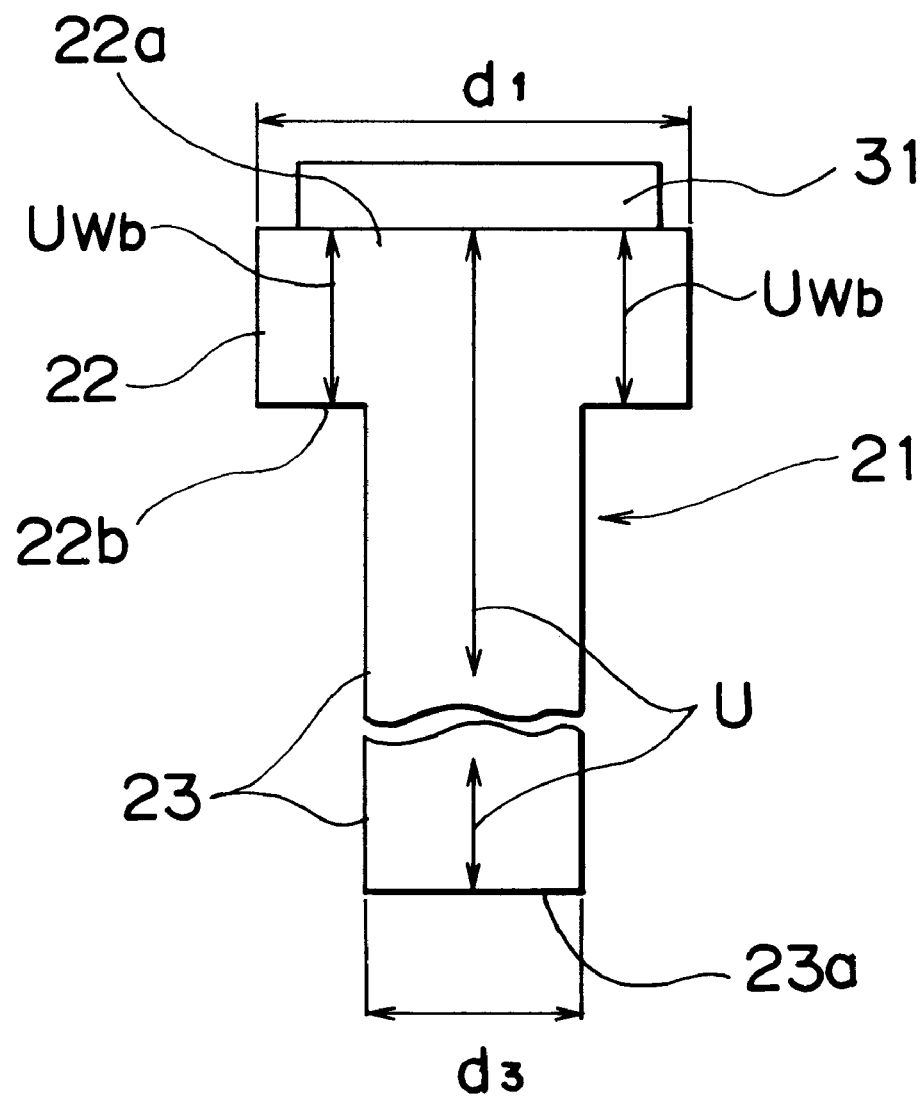
FIG. 5 is an explanatory view representing diffusion of the respective propagation path of the ultrasonic radiation and reflection thereof in a conventional bolt.
Figure 6:
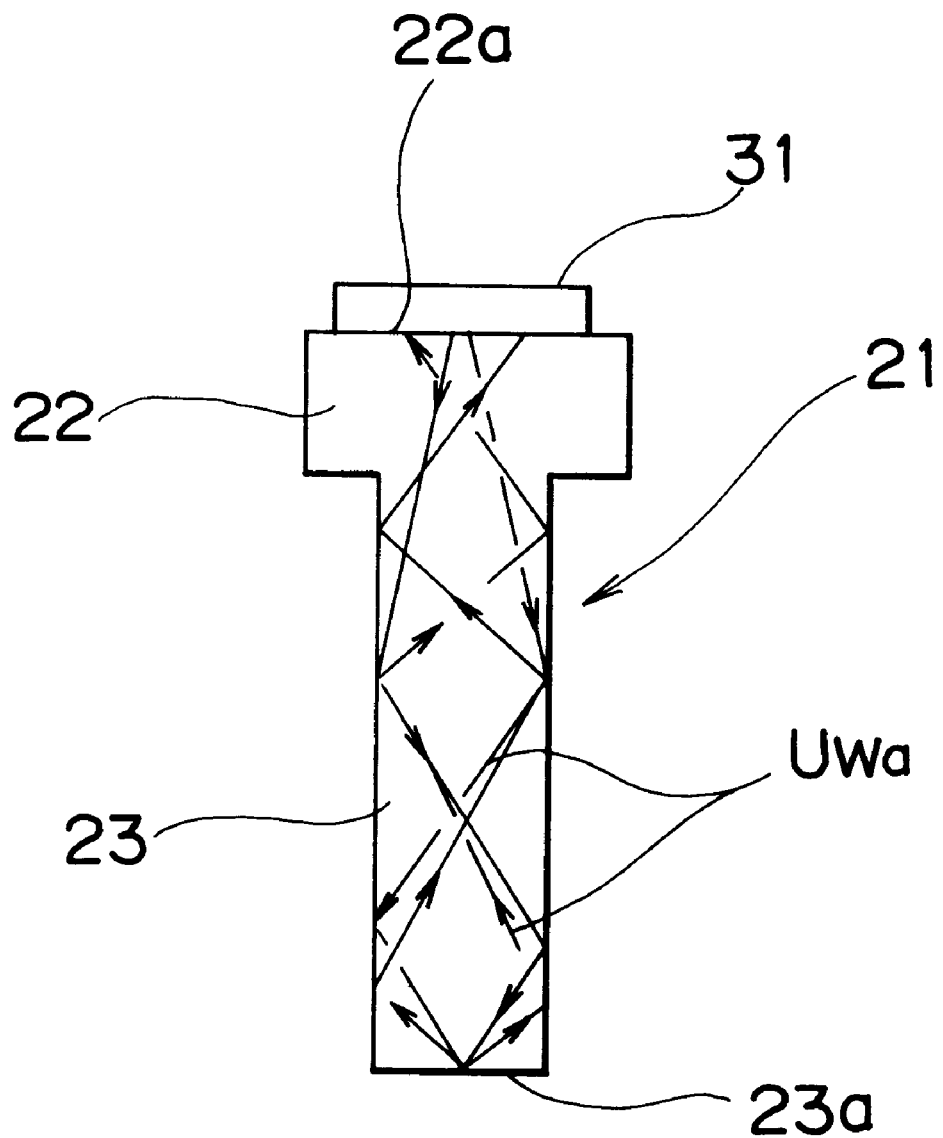
FIG. 6 is an explanatory view representing a state where ultrasonic radiation is reflected from radially extended portion of the head of the conventional bolt.
Figure 7:
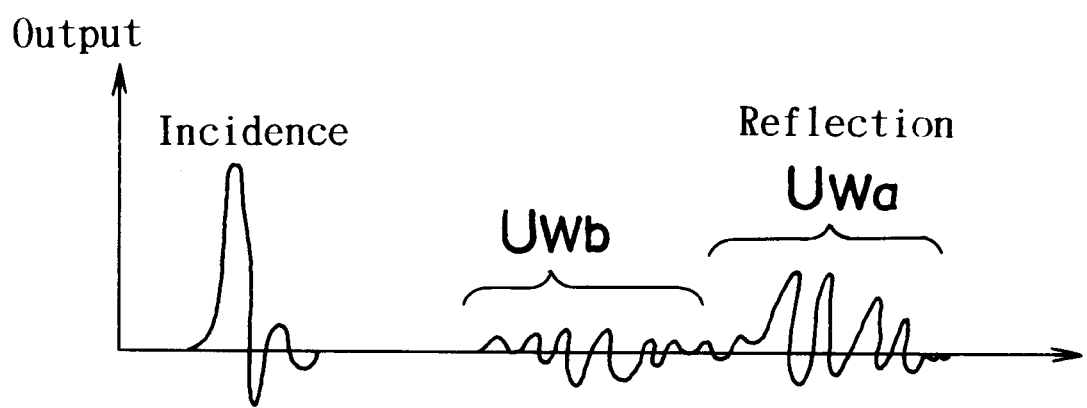
FIG. 7 is an explanatory view representing noise caused by reflection from the radially extended portion of the head portion of the conventional bolt, which cannot be distinguished from those reflected from the bottom surface of the axial portion among plurality of detected reflections, in the case where both the head portion and axial portion of the conventional bolt have flat end surfaces.

Referring to FIG. 4, another embodiment of the bolt according to the present invention will be described in detail. The codes in FIG. 4 identical to those of the preceding embodiment shall represent the elements identical or corresponding to those elements thereof In this embodiment, the curvature r2 of the curve formed on a top surface 2a of the head 2 of the aforementioned bolt 1 is different from the curvature r3 of the curve formed on a bottom surface 3a of the axial portion 3. Described below is how those curvatures are determined.

It is assumed that each top edge of the axial portion 3 is designated as F, I and each bottom edge thereof is designated as G, H in a state where the head 2 of the bolt 1 is seated to the object S, a center $C_2$ is defined as an intersection between a virtual line drawn from the F to H and a virtual line drawn from the I and G.

At a bottom of the axial portion 3, a curve is formed as a partial circumference with a curvature r4 having a radius equal to a distance from the center $C_2$ to G. At a top of the head 2 of the bolt 1, a curve is formed as a partial circumference with a curvature r5 having a radius equal to a distance from the center $C_2$ to E as the intersection between the top surface of the head 2 and a virtual line extending from the point F. Therefore ultrasonic radiation applied from the piezoelectric element 11 is converged at a curve of the top surface 2a of the head 2 of the bolt and further diffused through the axial portion 3. Then the reflection at the curve of the bottom surface 3a of the axial portion 3, likewise, is converged and diffused back to the piezoelectric element 11.

In this embodiment, the curve with the curvature r5 formed on the top surface 2a of the head 2 of the bolt 1 especially serves as an ultrasonic lens for converging ultrasonic radiation applied from the piezoelectric element 11 so as to be diffused through the axial portion 3 of the bolt 1 without causing interference with an end portion (corresponding to F and I of FIG. 4) of the insertion hole of the object S through which the bolt 1 is threaded. Likewise reflection from the curve with the curvature r4 formed as the bottom surface 3a of the axial portion 3 is converged and diffused back to the piezoelectric element 11 without causing interference with an end portion (corresponding to F and I of FIG. 4) of the insertion hole of the object S through which the bolt 1 is threaded. The reflection finally detected by the piezoelectric element 11 is brought into well converged state. This may improve accuracy for measuring the axial force and allow each curvature of both end surfaces to be defined by the length of the axial portion 3 of the bolt 1 and the height of the head 2 of the bolt 1, resulting in improved degree of design freedom.

It is obvious, in this embodiment, that the curved surface formed on the top surface 2a of the head 2 of the bolt 1 with the curvature r5 does not have to be formed over a whole top surface of the head 2 of the bolt 1. It may be formed across the curve extending from the point E to J as shown in FIG. 4.

What is claimed is:

1. A bolt comprising:

a head portion having a first spherical end surface with a first radius of curvature;

an axial portion having a second spherical end surface opposite from said first spherical end surface, said second spherical end surface having a second radius of curvature;

wherein a sum of the first radius of curvature and the second radius of curvature is equal to a distance between the first spherical end surface and the second spherical end surface, and wherein the second radius of curvature is equal to a half-length of a virtual diagonal line drawn in a longitudinal sectional area of the axial portion with respect to a longitudinal axis of the bolt.

2. A bolt according to claim 1, in combination with an ultrasonic device for applying ultrasonic radiation to said bolt.

3. A bolt according to claim 2, wherein said ultrasonic device is mounted to said first spherical end surface of said head portion.

4. A bolt according to claim 3, wherein said ultrasonic device includes a spherical surface having a radius of curvature substantially equal to said first radius of curvature of said first spherical end surface of said head portion.

5. A bolt according to claim 2, wherein said ultrasonic device has a size equal to or less than a diameter of said second spherical end surface of said axial portion of said bolt.

6. A bolt according to claim 2, further comprising an ultrasonic processing device for causing said ultrasonic device to generate ultrasonic radiation such that a signal processing is executed through detection of reflection.

7. A bolt according to claim 2, wherein said ultrasonic device is also for detecting ultrasonic radiation reflected from said bolt.

* * * * *